(12) United States Patent
Satyanarayana et al.

(10) Patent No.: US 9,156,756 B2
(45) Date of Patent: Oct. 13, 2015

(54) EFFICIENT PROCESS TO INDUCE ENANTIOSELECTIVITY IN PROCARBONYL COMPOUNDS

(75) Inventors: Chava Satyanarayana, Hyderabad (IN); Bollu Ravindra Babu, Hyderabad (IN)

(73) Assignee: Laurus Labs Private Limited, Hyderabad (Andhra Pradesh) (IN)

( * ) Notice: Subject to any disclaimer, the term of this patent is extended or adjusted under 35 U.S.C. 154(b) by 0 days.

(21) Appl. No.: 12/667,985

(22) PCT Filed: Jul. 30, 2008

(86) PCT No.: PCT/IN2008/000476
§ 371 (c)(1),
(2), (4) Date: Jan. 6, 2010

(87) PCT Pub. No.: WO2009/095931
PCT Pub. Date: Aug. 6, 2009

(65) Prior Publication Data
US 2010/0286408 A1    Nov. 11, 2010

(30) Foreign Application Priority Data
Jan. 31, 2008   (IN) .............................. 262/CHE/2008

(51) Int. Cl.
C07D 265/18     (2006.01)
C07C 29/42      (2006.01)
C07F 1/00       (2006.01)
C07F 3/00       (2006.01)

(52) U.S. Cl.
CPC .............. C07C 29/42 (2013.01); C07D 265/18 (2013.01); C07F 1/005 (2013.01); C07F 3/003 (2013.01)

(58) Field of Classification Search
CPC .............................. C07D 265/18; C07C 29/42
See application file for complete search history.

(56) References Cited

U.S. PATENT DOCUMENTS

| 5,519,021 A | 5/1996 | Young et al. |
| 5,633,405 A | 5/1997 | Thompson et al. |
| 6,015,926 A | 1/2000 | Chen et al. |
| 7,434,900 B2 | 10/2008 | Slomianny et al. |
| 7,439,400 B2 * | 10/2008 | Jiang et al. ..................... 564/413 |
| 2006/0217552 A1 | 9/2006 | Jiang et al. |

FOREIGN PATENT DOCUMENTS

WO    2011000532 A2    1/2011

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Tan et al. Angew. Chem. Int. Ed. 1999, 38, 711-713.*
MSDS for diethylzinc obtained from Akzo Nobel Polymer Chemicals, issued 1999.*
Hornbeck, J. M. Organic Chemistry, 2nd Edition, Thomson Brooks/Cole, 2005.*
Chen, et al., "Chemical Process Evolution of Efavirenz, a Potent Non-Nucleosidal HIV Reverse Transcriptase Inhibitor," Enantiomer, 1999, pp. 599-608, vol. 4.
Amadji, et al., "Enantioselective Dehydrohalogenation Using Chiral Alkoxides: Design of a Catalytic System Allowing Access to Axially Dissymmetric Compounds," The Journal of Organic Chemistry, 1998, pp. 5541-5546, vol. 63.
Lee, "Organometallic Compounds," Concise Inorganic Chemistry (5th Edition), 1999, p. 850.
Smith, et al., "Acids and Bases," March's Advanced Organic Chemistry: Reactions, Mechanisms and Structure (6th Edition), 2007, pp. 358 to 364.
Almenningen, et al., "The Molecular Structures of Dimethyl-, Diethyl- and Dipropylzinc Determined by Gas Phase Electron Diffraction. Normal Coordinate Analysis and ab initio Molecular Orbital Calculations on Dimethylzinc," Acta Chemica Scandinavica, 1982, pp. 159-166, vol. 36.
Jiang, et al., "Zn(II)-Mediated Alkynylation-Cyclization of o-Trifluoroacetyl Anilines: One-Pot Synthesis of 4-Trifluoromethyl-Substituted Quinoline Derivatives," The Journal of Organic Chemistry, 2002, pp. 9449-9451, vol. 67, No. 26.
Jiang, et al., "Alkynylation of Carbonyl Compounds with Terminal Acetylenes Promoted by ZnCl2 and Et3N: Simple, Mild and Efficient Preparation of Propargylic Alcohols," Tetrahedron Letters, 2002, pp. 8323-8325, vol. 43.
Jiang, et al., "Highly Enantioselective Alkynylation of Aldehydes Catalyzed by a Readily Available Chiral Amino Alcohol-Based Ligand," Chemical Communications, 2002, pp. 1524-1525.
Kobetz, et al., "Preparation of Sodium Hydride Complexes of Diethylzinc and Zinc Chloride," Inorganic Chemistry, 1963, p. 859, vol. 2, No. 4.
Bolm et al., "Asymmetric, Catalytic Phenyl Transfer to Aldehydes: Enantioselective Synthesis of Diarylmethanols," Chem. Int. Ed., 2000, vol. 39, No. 19, pp. 3645-3647.
Rudolph et al., "The MPEG Effect: Improving Asymmetric Processes by Simple Additives," J. Org. Chem., 2004, pp. 3997-4000.
Studte et al., "Zinc-Catalyzed Enantiospecific $sp^3$-$sp^3$Cross-Coupling of α-Hydroxy Ester Triflates with Grignard Reagents," Chem. Int. Ed., 2008, pp. 5451-5455.
Cote et al., "General Method for the Expedient Synthesis of Salt-Free Diorganozinc Reagents Using Zinc Methoxide," J. Am. Chem. Soc., 2008, pp. 2771-2773.
Armstrong et al., "Expanding Mg—Zn Hybrid Chemistry: Inorganic Salt Effects in Addition Reactions of Organozinc Reagents to Trifluoroacetophenone and the Implications for a Synergistic Lithium—Magnesium—Zinc Activation," Chem. Eur. J., 2011, vol. 17, pp. 8333-8341.

(Continued)

Primary Examiner — Joseph Kosack
Assistant Examiner — Matthew Coughlin
(74) Attorney, Agent, or Firm — Blank Rome LLP

(57) ABSTRACT

An efficient method to induce the enantioselectivity in procarbonyl compounds using chiral organometallic complexes. The present invention is also described a method for producing organo metallic complexes using a base and a metal halide.

4 Claims, No Drawings

(56) References Cited

OTHER PUBLICATIONS

Krasovskiy et al., "A LiCl-Mediated Br/Mg Exchange Reaction for the Preparation of Functional Aryl- and Heteroarylmagnesium Compounds from Organic Bromides," Chem. Int. Ed., 2004, vol. 43, pp. 3333-3336.

Krasovskiy, et al., "Mixed Mg/Li Amides of the Type $R_2NMgCl \cdot LiCl$ as Highly Efficient Bases or the Regioselective Generation of Functionalized Aryl and Heteroaryl Magnesium Compounds," Chem. Int. Ed., 2006, vol. 45, pp. 2958-2961.

Jin et al., "Revelation of the Difference between Arylzinc Reagents Prepared from Aryl Grignard and Aryllithium Reagents Respectively: Kinectic and Structural Features," J. Am. Chem. Soc., 2009, pp. 16656-16657.

Seebach et al., "Structure and Reactivity of Lithium Enolates, From Pinacolone to Selective *C*-Alkylations of Peptides. Difficulties and Opportunities Afforded by Complex Structures," Chem. Int. Ed. Engl., vol. 27, 1988, pp. 1624-1654.

Seebach et al., "Titanate-Catalyzed Enantioselective Addition of Dialkylzinc Compounds-Generated in situ from Grignard Reagents in Ether-to Aldehydes," Chem. Int. Ed. Engl., vol. 30, No. 8, 1991, pp. 1008-1009.

Weber et al., "Enantiomerically Pure Tertiary Alcohols by TADDOL-Assisted Additions to Ketones-or How to Make a Grignard Reagent Enantioselective," Chem. Int. Ed. Engl., vol. 31, No. 1, 1992, pp. 84-86.

Weber et al., "Ti-TADDOLate-Catalyzed, Highly Enantioselective Addition of Alkyl- and Aryl-Titanium Derivatives to Aldehydes," Tetrahedron, vol. 50, No. 25, 1994, pp. 7473-7484.

Soai et al., "Enantioselective Phenylation of Prochiral Aldehydes Using a Kinetically Formed Chiral Complex Between Grignard-Zinc Halide Reagent and *N,N*-Dibutyl-norephedrine," J. Chem. Soc., 1991, pp. 1013-1015.

Kim et al., "From Aryl Bromides to Enantioenriched Benzylic Alcohols in a Single Flask: Catalytic Asymmetric Arylation of Aldehydes," Chem. Int. Ed., 2006, pp. 4175-4178.

Salvi et al., "Catalytic Asymmetric Generation of (Z)-Disubstituted Allylic Alcohols," J. Am. Chem. Soc., 2007, pp. 16119-16125.

* cited by examiner

EFFICIENT PROCESS TO INDUCE ENANTIOSELECTIVITY IN PROCARBONYL COMPOUNDS

CROSS-REFERENCE TO RELATED APPLICATIONS

The present application claims the benefit of International Patent Application No. PCT/IN2008/000476, filed Jul. 30, 2008, which in turn claims priority to Indian Patent Application No. 262/CHE/2008, filed Jan. 31, 2008, the entire disclosures of both of which are incorporated by reference herein.

FIELD OF INVENTION

Present invention is directed towards the cost effective and industrially applicable process to induce enantioselectivity with improved yields. The present invention is also describes an improved process for making organometallic complexes.

BACKGROUND OF THE INVENTION

Asymmetric addition of organometallic compounds to carbonyls is a useful method for the production of chiral secondary/tertiary-alcohols. Typically for asymmetric synthesis, the active catalyst is generated in situ by the reaction of Lewis acid with chiral ligands. Addition of organometallic reagents to aldehydes and activated ketones has been achieved with excellent enantioselectivity. With inactivated ketones there has been some success, e.g., using salen 1 and camphanosulphonamide ligand 2.

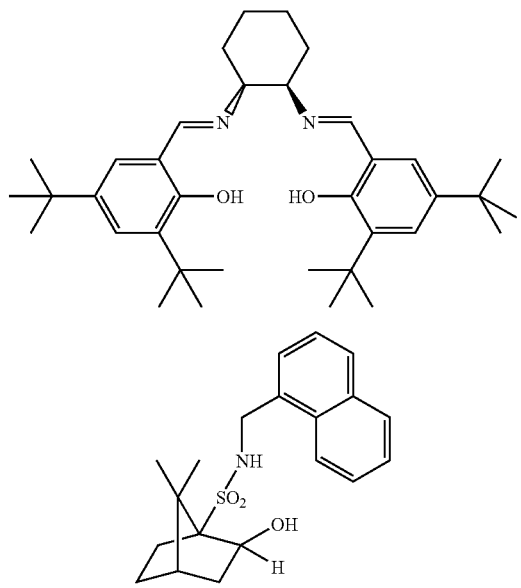

Generally, stoichiometric amount of the promoters [Lewis acid, e.g., $ZnR_2$ (R=alkyl/aryl), $Zn(OTf)_2$, $Cu(OTf)_2$, etc] is required for these asymmetric syntheses. Although, employing these promoters chiral alcohols has been obtained in high yields and ee upto 99%, they have limited applicability in industrial kale synthesis of the pharmaceutical intermediates, because they are expensive, difficult to store, difficult to handle, especially dialkyl zinc's are highly pyrophoric and require special modification to transfer the reagent. Moreover, the liberated byproduct methane/ethane (when using $ZnMe_2$/$ZnEt_2$) are a concern on industrial scale synthesis.

To overcome this problem, herein we report an efficient synthesis of active organometallic catalyst formed in situ from chiral auxiliaries and Metal halides. For example ephedrine zincate 3 was obtained by first deprotonation of alcohol (achiral auxiliary) and N-pyrollidene norephidrine (chiral auxiliary) with a base (e.g. NaH); to the resulting alkoxides was added zinc halides (scheme 1A). The advantages include the low cost of zinc halides, ease of storing, handling and transfer. Moreover, the byproduct (sodium halides) formed has no safety issues. Based upon this concept, other active catalysts were synthesized using chiral ligands (such as binols, amino alcohols, amino alcohol derivatives, ethylenediamine, alkylated ethylene diamines and ethylenediamine derivatives in combination with metal source based on zinc and copper (scheme 1).

Scheme-1

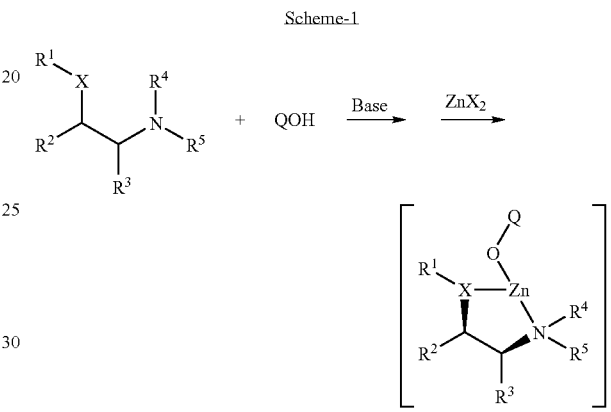

Scheme-1A

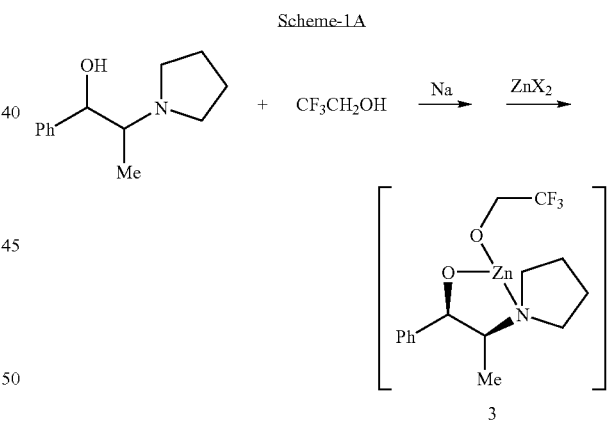

Using these chiral catalysts alkylation/alkynation of aldehydes afforded corresponding secondary alcohols (scheme-2), Scheme-2

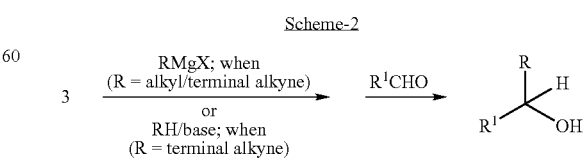

while addition to ketones/β-ketoesters afforded corresponding tertiary alcohols (scheme 3A and 3B).

Scheme-3A

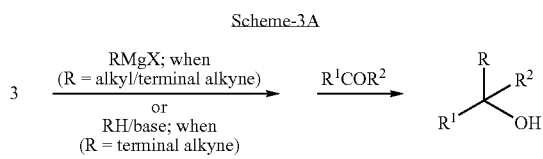

Scheme-3B

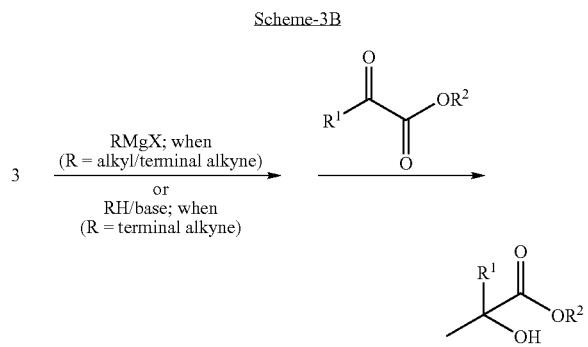

SUMMARY OF THE INVENTION

The main object of the present invention is to provide an improved process to make organometallic complexes using metal halides Another object of the present invention is to provide a process to induce the enantioselectivity in proketones.

Another object of the present invention is to provide a process to prepare an amino alcohol of formula

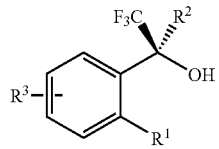

by the addition of (un) substituted alkane/alkyne ($R^2$) to a ketone using an organometallic complex Another object of the present invention is to provide an improved process to prepare organometallic complex without using Dialkyl zinc.

DETAILED DESCRIPTION OF THE INVENTION

In accordance with the present invention the main object is to prepare organometallic complex comprising the steps of;
Preparing the salts of chiral and/or achiral additives
Adding metal halide to the above obtained salts and converting to chiral and/or achiral metal complex
Adding Grignard reagent/lithium reagent or Zinc reagent etc, to the above chiral and/or achiral metal complex to form chiral organometal complex.
(or)
Adding terminal alkyne and a base to the above chiral metal complex to form chiral organometal complex.

The process as described above wherein metal salts of chiral and achiral additives are prepared by treating the chiral and/or achiral additives with a base selected from metal hydrides, metal alkoxides or metal hydroxides or organic bases such as DBU, HMDS, lower alkyl amines etc, and metal hydrides are more preferred.

The process as described above wherein the metal halide is a transitional metal halide and the most preferred metal halides are being Zinc and copper halides.

The process as described above wherein the Grignard reagent is selected from alkyl, alkenyl, alkynyl and aryl magnesium halides.

In a specific embodiment of the present invention is to provide an efficient method to induce the enantioselectivity in procarbonyl compounds and their enantiomers which are shown below;

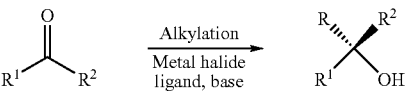

Wherein $R^1$ is
$C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, NH($C_1$-$C_6$-alkyl), N($C_1$-$C_6$-alkyl)$_2$, $CONH_2$, CONH($C_1$-$C_6$-alkyl), CON($C_1$-$C_6$-alkyl)$_2$, $NHCONH_2$, NHCONH($C_1$-$C_6$-alkyl), NHCON($C_1$-$C_6$-alkyl)$_2$, $CO_2$—$C_1$-$C_6$-alkyl, $C_3$-$C_7$-cycloalkyl, or $C_1$-$C_6$-alkoxy;
phenyl, biphenyl, or naphthyl, unsubstituted or substituted with one to four substituent selected from $R^3$, $R^4$, $R^5$, and $R^6$;
$R^3$, $R^4$, $R^5$, and $R^6$ are independently: halo (Cl, Br, F, I), $CF_3$, CN, $NO_2$, $NH_2$, NH($C_1$-$C_6$-alkyl), N($C_1$-$C_6$-alkyl)$_2$, $CONH_2$, CONH($C_1$-$C_6$-alkyl), CON($C_1$-$C_6$-alkyl)$_2$, $NHCONH_2$, NHCONH($C_1$-$C_6$-alkyl), NHCON($C_1$-$C_6$-alkyl)$_2$, aryl, $CO_2$—$C_1$-$C_6$-alkyl, $C_1$-$C_6$-alkyl, $C_2$-$C_6$-alkenyl, $C_2$-$C_6$-alkynyl, $C_3$-$C_7$-cycloalkyl, or $C_1$-$C_6$-alkoxy, such that $C_1$-$C_6$-alkyl is unsubstituted or substituted with aryl, aryl is defined as phenyl, biphenyl, or naphthyl, unsubstituted or substituted with $C_1$-$C_6$-alkyl, $C_1$-$C_6$-alkoxy, $NO_2$, or halo (Cl, Br, F, I);
$R^2$ is:
H
$C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, NH($C_1$-$C_6$-alkyl), N($C_1$-$C_6$-alkyl)$_2$, $CONH_2$, CONH($C_1$-$C_6$-alkyl), CON($C_1$-$C_6$-alkyl)$_2$, $NHCONH_2$, NHCONH($C_1$-$C_6$-alkyl), NHCON($C_1$-$C_6$-alkyl)$_2$, $CO_2$—$C_1$-$C_6$-alkyl, $C_3$-$C_7$-cycloalkyl, or $C_1$-$C_6$-alkoxy;
a. $C_1$-$C_4$-perfluoroalkyl,
R is:
$C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, NH($C_1$-$C_6$-alkyl), N($C_1$-$C_6$-alkyl)$_2$, $CONH_2$, CONH($C_1$-$C_6$-alkyl), CON($C_1$-$C_6$-alkyl)$_2$, $NHCONH_2$, NHCONH($C_1$-$C_6$-alkyl), NHCON($C_1$-$C_6$-alkyl)$_2$, $CO_2$—$C_1$-$C_6$-alkyl, $C_3$-$C_7$-cycloalkyl, or $C_1$-$C_6$-alkoxy;
comprising the steps of:
Preparing the salts of chiral and/or achiral additives
Adding metal halide to the above obtained salts and converting to chiral and/or achiral metal complex
Adding the Grignard reagent/lithium reagent or Zinc reagent etc, to the above chiral and/or achiral metal complex to form chiral organometal complex.

Adding the procarbonyl compounds to the chiral organometal complex

The process as described above wherein salts of chiral and achiral additives are prepared by treating the chiral and achiral additives with metal hydride or metal alkoxides or metal hydroxides or organic bases whereas metal hydrides are more preferred.

The process as described above wherein the metal halide is a transitional metal halide and the most preferred metal halides are being Zinc and copper halides.

The process as described above wherein the Grignard reagent is selected from alkyl, alkenyl, alkynyl and aryl magnesium halides.

The process as described above wherein the Lithium/Zinc reagent is selected from alkyl, alkenyl, alkynyl and aryl Lithium/Zinc reagents.

A further embodiment of the invention is the process for the preparation of an amino alcohol of formula:

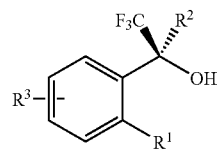

Wherein
$R^3$ is halo (Cl, Br, F, I)
$R^1$ is amino or substituted amino
$R^2$ is $C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, $NH(C_1$-$C_6$-alkyl), $N(C_1$-$C_6$-alkyl)$_2$, $CONH_2$, $CONH(C_1$-$C_6$-alkyl), $CON(C_1$-$C_6$-alkyl)$_2$, $NHCONH_2$, $NHCONH(C_1$-$C_6$-alkyl), $NHCON(C_1$-$C_6$-alkyl)$_2$, $CO_2$—$C_1$-$C_6$-alkyl, $C_3$-$C_7$-cycloalkyl, or $C_1$-$C_6$-alkoxy;
comprising the steps of:
Adding slowly an alkanol and chiral additive to a base in an organic solvent
Treating the above reaction mass with a metal halide to get chiral/achiral metal complex
Adding organometallic reagent of formula $R^2M$, wherein M represents Li, Zn or MgX; X is Cl, Br, I and F; to the metal complex to get an organometal complex
Mixing a carbonyl compound with the organometal complex to give the chiral alcohol.

The process as described above wherein the chiral additive is pyrrolidinyl norephidrine or its enantiomer or diastereomer.

The process as described above wherein the metal halide is a transitional metal halide and the most preferred metal halides are being Zinc and copper halides.

The process as described above wherein the base is selected from metal hydrides, metal alkoxides, metal hydroxides and organic bases.

The process as described above wherein the preferred metal hydride is sodium hydride.

The compounds of the present invention have asymmetric centers and this invention includes all of the optical isomers and mixtures thereof.

EXAMPLES

The present invention will now be further explained in the following examples. However, the present invention should not be construed as limited thereby. One of ordinary skill in the art will understand how to vary the exemplified preparations to obtain the desired results.

Example-1

Preparation of (S)-5-Chloro-α-(cyclopropylethynyl)-2-amino-α-(trifluoromethyl)benzene methanol

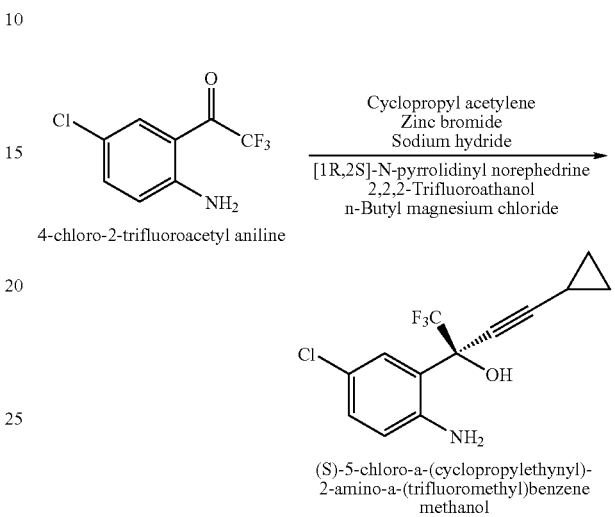

A solution of chloromagnesium-cyclopropylacetylide (CPA-MgCl) was prepared by adding neat cyclopropyl acetylene (3.62 g, 54.7 mmol) to a stirred solution of n-butyl magnesium chloride (2M solution in THF, 26.8 ml, 53.7 mmol) at 0-5° C. The solution was stirred for another 2 h at 0-5° C. In another dry flask, to anhydrous THF (80 ml) at 0-5° C., NaH (57% dispersion in mineral oil, 4.71 g, 117.7 mmol) was added slowly. The ice-bath was removed and the contents stirred at ambient temp for 30 min and cooled again to 0-5° C. 2,2,2-Trifluoroethanol (4.3 g, 3.13 ml, 42.9 mmol), and (1R, 2S)-pyrrolidinyl norephidrine (13.5 g, 65.8 mmol) were added and the resulting pale yellow solution was stirred at ambient temp for 60 min. A solution of zinc bromide (11.98 g, 54 mmol) in THF (40 ml) was added and the suspension was stirred for 60 min at 25-30° C. The solution of CPA-MgCl was then warmed to 25-30° C. and then transferred to the ephedrine zincate reagent by cannula, over 15 min., with THF (5 ml) as a wash, and the suspension was stirred for another 2 h. 4-Chloro-2-trifluoroacetylaniline (10 g, 44.7 mmol) was added in one portion to the reaction mixture and stirred for 15 h.

The reaction mixture was quenched with 30% aq $K_2CO_3$ (5.5 ml) and aged for 1 h. The solid material was filtered and washed with THF (5×10 ml). The combined filtrate concentrated to approx 10 ml under reduced pressure, toluene (100 ml) was added and sequentially washed with 30% citric acid (2×50 ml) and water (50 ml). The combined aqueous layer was back-extracted with toluene (25 ml) and saved for pyrrolidinyl norephidrine recovery. The combined organic phase was concentrated to approx 10 ml and hexane (50 ml) was added slowly with stirring. The mixture was cooled to 0° C., the solid was collected by filtration, washed with cold hexane (2×10 ml) and dried to give 10 g of pure (S)-5-Chloro-α-(cyclopropylethynyl)-2-amino-α-(trifluoromethyl)benzene methanol as a white solid.

Example-2

Preparation of (S)-5-Chloro-α-(cyclopropylethynyl)-2-amino-α-(trifluoromethyl)benzene methanol hydrochloride A solution of chloromagnesium-cyclopropylacetylide (CPA-MgCl) was prepared by adding neat cyclopropyl acetylene (3.62 g, 54.7 mmol) to a stirred solution of n-butyl magnesium chloride (2M solution in THF, 26.8 ml, 53.7 mmol) at 0-5° C. The solution was stirred for another 2 h at 0-5° C. In another dry flask, to anhydrous THF (80 ml) at 0-5° C., NaH (57% dispersion in mineral oil, 4.71 g, 117.7 mmol) was added slowly. The ice-bath was removed and the contents stirred at ambient temp for 30 min and cooled again to 0-5° C. 2,2,2-Trifluoroethanol (4.3 g, 3.13 ml, 42.9 mmol), and (1R,2S)-pyrrolidinylnorephidrine (13.5 g, 65.8 mmol) were added and the resulting pale yellow solution was stirred at ambient temp for 60 min. A solution of zinc bromide (11.98 g, 54 mmol) in THF (40 ml) was added and the suspension was stirred for 60 min at 25-30° C. The solution of CPA-MgCl was then warmed to 25-30° C. and then transferred to the ephedrine zincate reagent by cannula, over 15 min., with THF (5 ml) as a wash, and the suspension was stirred for another 2 h. 4-Chloro-2-trifluoroacetylaniline (10 g, 44.7 mmol) was added in one portion to the reaction mixture and stirred for 15 h.

The reaction mixture was quenched with 30% aq $K_2CO_3$ (5.5 ml) and aged for 1 h. The solid material was filtered and washed with THF (5×10 ml). The combined filtrate concentrated completely under reduced pressure. The residue was dissolved in isopropyl acetate (100 ml) and sequentially washed with 30% citric acid (2×50 ml) and water (50 ml). The combined aqueous layer was back-extracted with IPAc (25 ml) and saved for pyrrolidinylnorephidrine recovery. To the combined organic phase was added 12N HCl (4.1 ml). The resulting mixture was aged at 25-30° C. and then dried azeotropically and flushed with IPAc (2×25 ml). The slurry was aged for another 24 h at 25-30° C. and then filtered and washing was performed with cold IPAc (3×10 ml) and dried to afford 10 g of analytically pure (S)-5-Chloro-a-(cyclopropylethynyl)-2-amino-α-(trifluoromethyl)benzene methanol hydrochloride as a white solid.

Example-3

Preparation of (S)-5-Chloro-α-(cyclopropylethynyl)-2-amino-α-(trifluoromethyl)benzene methanol A solution of chloromagnesium-cyclopropylacetylide (CPA-MgCl) was prepared by adding neat cyclopropyl acetylene (36.2 g, 0.548 mol) to a stirred solution of n-butyl magnesium chloride (2M solution in THF, 268.0 ml, 0.535 mol) at 0-5° C. The solution was stirred for another 2 h at 0-5° C. In another dry flask, to anhydrous THF (300 ml) at 0-5° C., NaH (57% dispersion in mineral oil, (44.0 g, 0.916 mol) was added slowly. The ice-bath was removed and the contents stirred at ambient temp for 30 min and cooled again to 0-5° C. 2,2,2-Trifluoroethanol (43 g, 0.429 mol), and (1R,2S)-pyrrolidinyl norephidrine (135 g, 0.65 mol) were added and the resulting pale yellow solution was stirred at ambient temp for 60 min. Zinc chloride (73.1 g, 0.53 mol) was added in four lots and stirred for 60 min at 25-30° C. The solution of CPA-MgCl was then warmed to 25-30° C. and then transferred to the ephedrine zincate reagent, over 15 min., and the suspension was stirred for another 2 h. 4-Chloro-2-trifluoroacetylaniline (100 g, 0.447 mol) was added in one portion to the reaction mixture and stirred for reaction completion.

The reaction mixture was diluted with toluene (300 ml) and stirred for 1 h and quenched into 1M citric acid solution (1000 ml) and stirred for 10 min. Toluene layer was separated and washed with water (2×500 ml). The toluene layer was concentrated completely to give residue. The obtained residue was dissolved in methanol (300 ml) and isolated by adding DM water (450 ml).

Yield: 130 g

We claim:

1. A process for the preparation of an amino alcohol of formula:

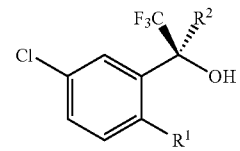

wherein
$R^1$ is amino;
$R^2$ is cyclopropylethynyl;
the process comprising the steps of:
slowly adding 2,2,2-trifluoroethanol and achiral additive to a base to form a reaction mass, wherein the chiral additive is selected from the group consisting of (1R,2S)-pyrrolidinyl norephidrine, its enantiomers, and diastereomers, and wherein the base is selected from the group consisting of metal hydrides, metal alkoxides and metal hydroxides in an organic solvent;
treating the reaction mass with a metal halide to obtain a chiral metal complex, wherein the metal halide is selected from the group consisting of zinc halide and copper halide;
adding an organometallic reagent of formula $R^2M$ to the chiral metal complex in a solvent to form a suspension, wherein M is Li or MgX, and X is a halo;
stirring the suspension to obtain a chiral organometal complex; and
mixing 4-chloro-2-trifluoroacetylaniline with the chiral organometal complex to produce the desired chiral amino alcohol.

2. The process of claim 1, wherein the metal hydride is sodium hydride.

3. The process of claim 1, wherein the metal halide is zinc chloride or zinc bromide.

4. The process of claim 1, wherein the organometallic reagent cyclopropylacetylide magnesium chloride.

* * * * *